United States Patent [19]
Pomplun et al.

[11] Patent Number: 5,972,805
[45] Date of Patent: Oct. 26, 1999

[54] ION SENSITIVE POLYMERIC MATERIALS

[75] Inventors: William Seal Pomplun, Neenah; Pavneet Singh Mumick, Appleton, both of Wis.; David Martin Jackson, Roswell, Ga.; Yihua Chang, Appleton, Wis.

[73] Assignee: Kimberly-Clark Worldwide, Inc., Neenah, Wis.

[21] Appl. No.: 09/056,470

[22] Filed: Apr. 7, 1998

[51] Int. Cl.$^6$ .................................................. B32B 27/00
[52] U.S. Cl. ........................ 442/59; 442/152; 442/155; 442/165; 442/166; 442/167; 442/168; 442/381; 442/400; 442/401; 525/176
[58] Field of Search ............................ 442/59, 152, 155, 442/165, 166, 167, 168, 381, 400, 401; 525/176

[56] References Cited

U.S. PATENT DOCUMENTS

| | | | |
|---|---|---|---|
| Re. 28,957 | 9/1976 | Drelich et al. | 442/102 |
| 3,406,688 | 10/1968 | Cubitt | 128/284 |
| 3,800,797 | 4/1974 | Tunc | 128/290 R |
| 3,804,092 | 4/1974 | Tunc | 128/284 |
| 3,897,782 | 8/1975 | Tunc | 128/290 |
| 3,939,836 | 2/1976 | Tunc | 128/284 |
| 4,005,251 | 1/1977 | Tunc | 536/59 |
| 4,035,540 | 7/1977 | Gander | 428/198 |
| 4,073,777 | 2/1978 | O'Neill et al. | 260/75 S |
| 4,084,033 | 4/1978 | Drelich | 428/198 |
| 4,084,591 | 4/1978 | Takebe et al. | 128/285 |
| 4,117,187 | 9/1978 | Adams et al. | 428/286 |
| 4,245,744 | 1/1981 | Daniels et al. | 206/812 |
| 4,258,849 | 3/1981 | Miller | 206/812 |
| 4,309,469 | 1/1982 | Varona | 428/74 |
| 4,343,403 | 8/1982 | Daniels et al. | 206/812 |
| 4,372,447 | 2/1983 | Miller | 206/812 |
| 4,419,403 | 12/1983 | Varona | 428/288 |
| 4,537,807 | 8/1985 | Chan et al. | 428/74 |
| 4,702,947 | 10/1987 | Pall et al. | 428/36 |
| 4,855,132 | 8/1989 | Heller et al. | 424/78 |
| 5,104,923 | 4/1992 | Steinwand et al. | 524/461 |
| 5,300,192 | 4/1994 | Hansen et al. | 162/184 |
| 5,312,883 | 5/1994 | Komatsu et al. | 526/318.44 |
| 5,317,063 | 5/1994 | Komatsu et al. | 525/330.2 |
| 5,384,189 | 1/1995 | Kuroda et al. | 428/288 |
| 5,500,281 | 3/1996 | Srinivasan et al. | 428/288 |
| 5,509,913 | 4/1996 | Yeo | 604/364 |

FOREIGN PATENT DOCUMENTS

| | | | |
|---|---|---|---|
| 0 303 528 | 2/1989 | European Pat. Off. | D21H 13/08 |
| 0 608 460 | 8/1994 | European Pat. Off. | D04H 1/64 |
| 0 726 068 | 8/1996 | European Pat. Off. | A61F 13/15 |
| 1-306661 | 12/1989 | Japan | D04H 1/58 |
| 5-179548 | 7/1993 | Japan | D04H 1/48 |
| 6-172453 | 6/1994 | Japan | C08F 220/06 |

OTHER PUBLICATIONS

American Society for Testing and Material (ASTM) Designation: D 5034–11 (1994), "Standard Test Method for Breaking Force and Elongation of Textile Fabrics (Grab Test)," p. 708.

*Primary Examiner*—Helen L. Pezzuto
*Attorney, Agent, or Firm*—Jones & Askew, LLP

[57] ABSTRACT

A water soluble polymer comprising from about 25 weight % to about 90 weight % of an unsaturated carboxylic acid/unsaturated carboxylic acid ester terpolymer; from about 10 weight % to about 75 weight % of a divalent ion inhibitor and from about 0 weight % to about 10 weight % of a plasticizer is soluble in an aqueous environment having a divalent ion concentration less than about 50 ppm and a monovalent ion concentration of less than about 0.5 weight %. Also disclosed is a water dispersible fibrous fabric having a fibrous substrate and an effective amount of the binder distributed on the substrate and a method of making a water dispersible fibrous fabric.

22 Claims, No Drawings

ION SENSITIVE POLYMERIC MATERIALS

BACKGROUND OF THE INVENTION

The present invention relates to a water dispersible material whose solubility in water is dependent upon the total ionic concentration in the water and particularly the concentration of divalent ions. More particularly, the invention relates to a polymer binder composition that is dispersible in water when the concentration of divalent ions in the water is less than about 50 parts per million (ppm) and desirably, the concentration of monovalent ions is less than about 0.5 weight %. Advantageously, the polymer composition is insoluble in an aqueous solution having a concentration of a divalent ions greater than about 50 ppm. The invention is further directed to a method of making a water dispersible nonwoven fibrous fabric comprising a fibrous substrate and the ion sensitive binder composition distributed therein and the water dispersible nonwoven fibrous fabric utility in water-dispersible personal care products.

While the composition and products of the present invention are described herein primarily in connection with advantageous applications as a disposable absorbent article and more particularly, a premoistened wipe, it should be understood that the present invention is not limited thereto. In light of the present disclosure, those skilled in the art will recognize a variety of applications in other fields where flushability of a fibrous fabric would be desirable.

Nonwoven fibrous fabrics and webs are widely used as components of disposable products as sanitary napkins, diapers, wound dressings, bandages, nursing pads, and premoistened wipes. The terms "nonwoven fibrous webs", "fibrous webs", "nonwoven fabrics", "fabrics" and "fibrous substrates" are interchangeably used herein and include, without limitation, methods of making such fabrics and webs as meltblowing, melt spinning, air-laying and wet laying.

Such fabrics, if they are to function effectively, must maintain their structural integrity, as well as exhibit satisfactory tensile strength when they are wet or damp. However, it has been recognized that if such nonwoven fabrics were to lose substantially all of their tensile strength when exposed to water and become readily dispersible therein, disposal problems would be substantially eliminated. The products could be easily and conveniently flushed down a conventional toilet (water closet).

Desirably, the fabrics possesses a number of characteristics such as softness and flexibility. The fabric is usually formed by wet or dry laying a random plurality of fibers and joining them together to form a coherent web. Unfortunately, in an attempt to provide nonwoven fabrics having certain in-use characteristics, prior methods have rendered the fabric nondispersible in water. For example, nonwovens have been bonded with fluid-insoluble resins which impart in-use strength. However, such resins impede flushing the fabric by rendering the fabric substantially water insoluble.

With regard to premoistened wipes, special problems arise. The wipes, which are used for skin cleansing, and are known commercially as towelettes, wet wipes or fem-wipes, are formed from paper or nonwoven fibrous webs treated with a polymeric binder. The binder imparts to the web a degree of wet strength so that the web will not lose its tensile strength while being stored in an appropriate liquid medium. However, after the wipe has been used, the binder should be readily weakened when exposed to an aqueous environment, such as a toilet, without clogging the toilet and plumbing.

So far, various binders have been used in the manufacture of a wipe. For example, wipes have included as a binder an acid-insoluble, alkali-soluble polymeric polycarboxylic acid and functional derivatives thereof wherein the acid is placed in water and enough alkali is added to substantially neutralize all acidic groups prior to applying the binder to the web. The binder-saturated web is dried and then immersed in a low pH medium where it retains its structural integrity yet will still break up when the wipe is immersed in a sufficiently high pH liquid medium.

Another binder used for a premoistened wipe has been polyvinyl alcohol combined with a gelling or insolubilizing agent such as borax. The borax crosslinks at least the surface of the polymer binder before drying the web to give a water resistant web. Such cross-links are reversible, that is, when the concentration of borax is reduced below a certain level, the degree of cross-linking is so low that the binder becomes soluble in water. However, boron-containing solutions are unacceptable for personal care products due to safety concerns.

Yet another water dispersible nonwoven fabric has used a water soluble binder comprising an unsaturated carboxylic acid/unsaturated carboxylic acid ester copolymer. A problem with the above binders is that to prevent the nonwoven fibrous fabric from disintegrating prior to disposal, the wipe must be maintained in a solution having a pH which may cause irritation to the skin when the wipe is used.

The above binders containing carboxylic acid groups have worked well for making a water dispersible fibrous web that is, to a limited degree, water soluble, water dispersible or water disintegratable in an aqueous environment, provided the water is predominantly void of divalent ions. However, in those areas where the water is "moderately hard", because the water contains divalent ions such as calcium ions or magnesium ions, the wipes do not readily disperse. The water soluble polymeric binder is substantially rendered insoluble by the presence of divalent ions. Although not wanting to be held to any particular theory, it is believed that the divalent ions crosslink the binder, preventing it from dispersing in the water. Until now, it has not been recognized the adverse effect that divalent ions present in the aqueous environment has on the water solubility of the polymeric binder.

Accordingly, there is a need for a water soluble binder composition that can be used in an article, such as a wipe, that is safe to use and will be substantially unaffected by the presence of divalent ions normally found in moderately hard water.

SUMMARY OF THE INVENTION

Briefly, the present invention relates to a water soluble polymeric binder composition that can be used in a nonwoven fibrous web, fabric or substrate. The water soluble polymeric binder composition has from about 25 weight % to about 90 weight % of an unsaturated carboxylic acid/unsaturated carboxylic acid esters/ester copolymer; from about 10 weight % to about 75 weight % of a divalent ion inhibitor; and can have from about 0 weight % to about 10 weight % of a plasticizer. Advantageously, the water soluble binder composition is soluble in an aqueous environment having a divalent ion concentration less than about 50 ppm and a monovalent concentration of less than about 0.5 weight %. As used herein "divalent ion inhibitor" means any substance which inhibits the irreversible cross-linking of the acrylic acid units in the base copolymer by the divalent ions.

Another aspect of the invention is a nonwoven fibrous fabric that is water dispersible. The nonwoven fabric includes a fibrous substrate and the water soluble binder distributed through the fibrous substrate for binding together the fibrous material of the fabric. The nonwoven fibrous fabric is water dispersible in an aqueous environment having a divalent ion concentration of less than about 50 ppm and a monovalent ion concentration of less than about 0.5 weight %.

Another aspect of the invention is a method of making a water dispersible nonwoven fibrous fabric. The method includes the steps of contacting a fibrous substrate with an effective amount of the water soluble binder so as to bind a substantial amount of the fibers and drying the fabric. The binder comprises from about 25 weight % to about 90 weight % of an unsaturated carboxylic acid/unsaturated carboxylic acid ester copolymer; from about 10 weight % to about 75 weight % of a divalent ion inhibitor; and from about 0 weight % to about 10 weight % of a plasticizer, and wherein the water soluble binder composition is soluble in an aqueous environment having a divalent ion concentration less than about 50 ppm and a monovalent ion concentration of less than about 0.5 weight %.

It is an object of the invention to provide a water soluble polymer which is soluble in soft to moderately hard water but will be insoluble in water having concentrations of divalent ions greater than about 50 ppm. As used herein "moderately hard" water means water which possess a total concentration of from about 25 ppm to about 50 ppm of divalent ions. Non-limiting examples of divalent ions include calcium and/or magnesium ions. One will understand that soft water has a concentration of divalent ions of less than about 25 ppm and very hard water has a concentration of divalent ions of more than about 50 ppm.

It is another object of the invention to provide a nonwoven fabric that is water dispersible in soft to moderately hard water having a concentration of divalent ions of less than about 50 ppm.

Another object of the invention is to provide a premoistened wipe that is easily dispersible in soft to moderately hard water.

It is another object of the invention to provide a wipe that can be disposed of in standard sewer or septic systems that is water dispersible and will not clog the water closet or plumbing.

DESCRIPTION OF THE PREFERRED EMBODIMENTS

The nonwoven fabrics prepared in accordance with this invention have good dry tensile strength depending upon, among other things, the amount of binder applied to the fabric and the manner in which it is applied. The nonwoven fabric is abrasion resistant and retains significant tensile strength in aqueous solutions containing greater than about 50 ppm divalent ions. Yet the nonwoven fabric is readily dispersible in soft to moderately hard water. Because of this latter property, nonwoven fabrics of the invention are well suited for disposable products such as sanitary napkins, diapers, and dry and premoistened wipes which can be thrown in a flush toilet after use.

The binder of the present invention provides for the breaking up of the wipe during flushing because in tap water the binder loses bonding strength between the binder and the fibers. However, the binder has substantial adhesive strength to hold the nonwoven fabric together during the shelf life period and during its use. In accordance with one embodiment of the invention, the water-soluble binder composition comprises from about 25 weight % to about 90 weight % of unsaturated carboxylic acid/unsaturated carboxylic acid esters terpolymer and from about 10 weight % to about 75 weight % of a divalent ion inhibitor. Optionally, the binder can include from 0 weight % to about 10 weight % of a plasticizer to impart a desired softness to the final nonwoven fabric. Desirably, the water-soluble binder composition includes from about 40 weight % to about 75 weight % of unsaturated carboxylic acid/unsaturated carboxylic acid/ester copolymer and from about 25 weight % to about 60 weight % of the divalent ion inhibitor. The binder composition of the invention is water soluble in an aqueous environment having a divalent ion concentration less than about 50 ppm and a monovalent ion concentration of less than about 0.5 weight %.

Although conventional unsaturated carboxylic acids can be used as a monomer component of the copolymers, acrylic acid and/or methacrylic acid are preferable. Examples of the unsaturated carboxylic acid ester monomer components include acrylic esters and/or methacrylic esters having an alkyl group of 1 to 18 carbon atoms or a cycloalkyl group of 3 to 18 carbon atoms and it is preferable that acrylic esters and/or methacrylic esters having an alkyl group of 1 to 12 carbon atoms or a cycloalkyl group of 3 to 12 carbon atoms be used singly or in combination.

More specifically, examples of the copolymers include copolymers of 10 to 90%, preferably 20 to 70% by weight of acrylic acid and/or methacrylic acid and 90 to 10%, preferably 80 to 30% by weight of acrylic esters and/or methacrylic esters having an alkyl group of 1 to 18 carbon atoms or a cycloalkyl group of 3 to 18 carbon atoms in which 1 to 60 mole %, preferably 5 to 50 mole % of acrylic acid and/or methacrylic acid is neutralized to form a salt; or copolymers of 30 to 75%, preferably 40 to 65% by weight of acrylic acid, 5 to 30%, preferably 10 to 25% by weight of acrylic esters and/or methacrylic esters having an alkyl group of 8 to 12 carbon atoms and 20 to 40%, preferably 25 to 35% by weight of acrylic esters and/or methacrylic esters having an alkyl group of 2 to 4 carbon atoms in which 1 to 50 mole %, preferably 2 to 40 mole % of acrylic acid is neutralized to form a salt. The molecular weight of the copolymers are not particularly limited, although the weight-average molecular weight of the terpolymers is preferably 5,000 to 1,000,000, more preferably 30,000 to 500,000.

Any inorganic base or organic base can be optionally used as a neutralizing agent to neutralize the unsaturated carboxylic acid component of the copolymers. Examples of the neutralizing agents include inorganic bases such as sodium hydroxide, potassium hydroxide, lithium hydroxide and sodium carbonate, and amines such as monoethanolamine, diethanolamine, diethylaminoethanol, ammonia, trimethylamine, triethylamine, tripropylamine, morpholine. Preferred are ethanolamines or sodium hydroxide or a combination of potassium hydroxide and ethanolamines. Unsaturated carboxylic acid/unsaturated carboxylic acid ester copolymers are disclosed in U.S. Pat. No. 5,384,189 entitled "WATER-DECOMPOSABLE NON-WOVEN FABRIC" entire disclosure of which is incorporated herein by reference and made a part hereof. Several such copolymers are available from the LION Corporation, Tokyo Japan.

Divalent ion inhibitors useful in the invention include sulfonated copolyesters such as EASTMAN AQ 29D, AQ 38D and AQ 55D (available from Eastman Chemicals, Kingsport, Tenn.); L9158 (available from ATO Findley); polyphosphates such as sodium tripolyphosphate, phosphonic acids such as ethylene diaminetetra (methylenephosphonic acid), aminocarboxylic acids such as ethylenediaminetetraacetic acid and nitrilotriacetic acid, hydroxycarboxylic acids such as citric acid; and polyamines such as porphozins.

In another embodiment of the invention, the binder formulations of the present invention can be applied to any fibrous substrate to form a water dispersible fibrous fabric. The water dispersible fibrous fabric of the invention is soluble, i.e. disintegratable or dispersible, in an aqueous environment having a divalent ion concentration less than about 50 ppm and a monovalent ion concentration of less than about 0.5 weight %. The water dispersible fabric of the invention is particularly suitable for use in a water-dispersible product. Suitable fibrous substrates include, but are not limited to, nonwoven and woven fabrics. In many embodiments, particularly personal care products, preferred substrates are nonwoven fabrics due to their absorptivity of fluids such as blood, menses and urine. As used herein "nonwoven fabric" refers to a fabric that has a structure of individual fibers or filaments randomly arranged that may be bonded together in a mat-like fashion. Nonwoven fabrics can be made from a variety of processes including, but not limited to, air-laid process, wet-laid processes, hydroentangling processes, staple fiber carding, bonding and solution spinning.

The binder formulations are particularly useful for binding fibers of air-laid nonwoven fabrics. These air-laid materials are particularly useful for body-side liners, fluid distribution materials, fluid in-take materials, such as a surge material, absorbent wrap sheet and cover stock for various water-dispersible personal care products. Air-laid materials are particularly useful for use as a premoistened wipe. The basis weights for these air-laid non-woven fabrics will range from about 20 to about 200 grams per square meter (gsm). Surge or in-take materials need better resiliency and higher loft so staple fibers having about 6 denier or greater are used to make these products. A desirable final density for the surge or in-take materials is between about 0.025 grams per cubic centimeter (g/cc) to about 0.050 g/cc. Fluid distribution materials will have a higher density, in the desired range of about 0.10 to about 0.20 g/cc using fibers of lower denier, most desirable fibers have a denier of less than about 1.5.

The nonwoven fabric itself can be formed of natural fibers, synthetic fibers and combinations thereof. The choice of the fibers depends upon, for example, fiber cost and the intended end use of the finished fabric. Non-limiting examples of suitable fibrous substrates which can be used alone or in any combination include cotton, linen, jute, hemp, wool, wood pulp, regenerated cellulosic fibers such as viscose rayon, modified cellulosic fibers such as cellulose acetate, or synthetic fibers derived from polyvinyl alcohol, polyesters, polyamides, polyacrylics, etc. Blends of one or more of the above fibers may also be used if so desired.

Desirably, the nonwoven fabric is formed from relatively short fibers, such as wood pulp fibers. The minimum length of the fibers depends on the method selected for forming the nonwoven fabric. Where the nonwoven fabric is formed by the wet or dry method the fiber length is desirably from about 0.1 millimeters to 15 millimeters. It has been determined that when a substantial quantity of fibers having a length greater than about 15 millimeters is placed in a flushable fabric their length tends to form ropes of fibers which are undesirable in a flushable material. Desirably, the nonwoven fabric of the invention has a relatively low wet cohesive strength when they are not bonded together by an adhesive or binder material. When such nonwoven fabrics are bonded together by an adhesive which loses its bonding strength in tap water and in sewer water, the fabric will break up readily by the agitation provided by flushing and moving through the sewer pipes.

The nonwoven fabric of the present invention may be formed from a single layer or multiple layers. In the case of multiple layers, the layers are generally positioned in a juxtaposed or surface-to-surface relationship and all or a portion of the layers may be bound to adjacent layers. The nonwoven fabric may also be formed from a plurality of separate nonwoven fabrics wherein the separate nonwoven fabrics may be formed from a single or multiple layers. The binder may be distributed on the nonwoven fabric as a single application or where there are multiple layers, each individual layer may be separately subjected to a binder application and then combined with other layers in a juxtaposed relationship to form the finished nonwoven fabric.

The binder composition may be applied to the nonwoven fabric by any known process of application. The binder can be applied to the nonwoven fabric by, for example, spraying, dipping, printing, coating, or any other technique. When the binder is applied to the nonwoven fabric so as to retain the integrity of the fabric, it is necessary to uniformly disperse the binder in substantially all of the fabric so as to cover substantially all of the fiber junctions.

Another embodiment of the invention is a method making a water dispersible nonwoven fabric. The method includes the steps of contacting the fibrous substrate with an effective amount of the binder formulations of the present invention so as to bind a substantial amount of the fibers and drying the fabric so as to form a water dispersible fibrous fabric. For ease of applying the binder to the nonwoven fabric, the binder may be emulsified, dispersed and/or dissolved in water or a solvent such as methanol, ethanol, or the like, with water being the preferred carrier. The binder has from about 1 weight % to about 30 weight % solids and more desirably, from about 2.5 weight % to about 20 weight % solids. As discussed above, plasticizers such as: glycerol; sorbitol; emulsified mineral oil; dipropyleneglycoldibenzoate; polyglycols such as, polyethylene glycol, polypropylene glycol and copolymers thereof; decanoyl-N-methylglucamide; tributyl citrate; and tributoxyethyl phosphate can be added to the solution containing the binder composition. The amount of plasticizers vary according to the desired softness of the nonwoven fabric but generally can be added in an amount of from 0 weight % to about 10 weight %.

Perfumes, colorants, antifoams, bactericides, bacteriostats, surface active agents, thickening agents, fillers, as well as other water-soluble binders such as polyvinyl alcohol, aqueous dispersions of, for example, polyvinyl chloride, polyacrylates, polymethacrylates, copolymers of acrylates and methacrylates, polymers of acrylic acid, methacrylic acid or a salt thereof and carboxymethylcellulose may also be incorporated into the binder if desired.

Based of the total weight of the fabric, the binder may be distributed or "added on" to the nonwoven fabric in an amount of from about 1 weight % to about 50 weight %, desirably, from about 5 weight % to about 30 weight % and more desirably, from about 8 weight % to about 25 weight %. Where the amount of the binder is less than the amount mentioned above, the resulting non-woven fabric has insufficient mechanical strength. Alternatively, where the amount of the binder is more than the amount mentioned above, the resulting non-woven fabric does not have high softness and good touch.

Once the binder composition is applied to the fabric, the fabric is dried by any conventional means. Once dry, the coherent fibrous fabric exhibits improved tensile strength when compared to the tensile strength of a similar but untreated wet-laid or dry-laid fabric. For example, the tensile strength of the fabric may be increased by at least 25 percent compared to the tensile strength of the untreated fabric. More particularly, the tensile strength of the fabric may be increased by at least about 100 percent and even more particularly the tensile strength of the fabric may be increased by at least about 500 percent as compared to an untreated fabric. However, and quite advantageously, the fabric will disintegrate or is disintegratable when placed in soft to moderately hard cold water and agitated. As used herein "disintegrate", "disintegratable" and "water dispersible" are used interchangeably to describe the breaking up or separating into multiple parts where after about 20 minutes and desirably, after about 10 minutes, in an aqueous environment (having a concentration of divalent ions of less than about 50 ppm), the fabric separates into multiple pieces each having an average size of less than about 50%, more desirably less than about 40%, and even more desirably less than about 30%, relative to the pre-dispersed size.

A nonwoven fabric suitable for conversion into a wipe or any other disposable product described above may be any of the type employed for such article. The finished wipes may be individually packaged, preferably in a folded condition, in a moisture proof envelope or packaged in containers holding any desired number of prefolded sheets and stacked in a water-tight package with a wetting agent applied to the wipe. The wetting agent may comprise, by weight, from about 10 percent to about 400 percent of the dry weight of the wipe itself. The wipe must maintain its desired characteristics over the time periods involved in warehousing, transportation, retail display and storage by the consumer. Accordingly, shelf life may range from two months to two years.

Various forms of impermeable envelopes for containing wet-packaged materials such as wipes and towelettes and the like are well known in the art. Any of these may be employed in packaging the premoistened wipes of the present invention.

The nonwoven fabric of the present invention can be incorporated into such body fluid absorbing products as sanitary napkins, diapers, surgical dressings, tissues and the like. The binder is such that it is not dissolved when contacted by such body fluids since the concentration of divalent ions in the fluids is above the level of dissolution. The nonwoven fabric retains its structure, softness and exhibits a toughness satisfactory for practical use. However, when brought into contact with water having a concentration of divalent ions of up to about 50 ppm the binder is dissolved. The nonwoven fabric structure is then easily broken and dispersed in the water.

The present invention will be illustrated by the following examples, which are not to be interpreted in any way as imposing limitations upon the scope of the invention described herein.

EXAMPLE 1

A binder solution was formulated having: 52.6 weight % of an unsaturated carboxylic acid/unsaturated carboxylic acid ester copolymer (available from LION Corporation, Tokyo, Japan under the tradename SSB-3b); 42.8 weight % of Code L9158 (available from ATO Findley, Wauwatosa, Wis.) as a divalent ion inhibiting agent; and 4.6 weight % of a non-crystallizing grade of Sorbitol (available from Pfizer) as a plasticizer was prepared by dissolving the resin in water to yield a solution containing about 26 weight % solids.

A fibrous substrate containing 86 gsm Weyerhauser NB420 pulp (80% softwood, 20% hardwood) was sprayed on both sides with 7 gsm of the above binder resulting in an overall basis weight of 100 gsm. The fabric had a density of about 0.03 g/cm$^3$, and bulk thickness of about 2 mm. The material was immersed in a small dish having 50 milliliters of a test solution comprising 0.85 weight % sodium chloride and 30 ppm calcium chloride. The test solution was prepared by first dissolving 8.3 grams of anhydrous $CaCl_2$ in 991.7 milliliters of deionized water to make a solution of 0.83% $CaCl_2$. Eighteen grams of NaCl and 20 grams of 0.83% $CaCl_2$ solution were added to 1962 milliliters of deionized water. The fabric was stable in the test solution. The fabric was found to be dispersible in cold tap water.

EXAMPLE 2

A fabric containing 28 gsm of lyocell fiber (3d/f, 6 millimeters in length, available from Courtaulds Coventry, U.K.) was sprayed on one side with 8 gsm of the binder of Example 1. The fabric had an overall basis weight of 36 gsm. It was recognized that some pulp fiber having length of 0.1 mm to about 2 millimeters would be necessary to achieve good fiber formation. This material was found to be dispersible in cold tap water.

EXAMPLE 3

A fabric containing 40 gsm of Cemfiber polypropylene (2d/f and 6 millimeters in length available from Cemfiber a/s Varde Denmark) and Rayonier pulp (75:25 blend, respectively) was sprayed with 10 gsm of the binder of Example 1 to provide a fabric with overall basis weight of 50 gsm. This was repeated but with the fabric and binder having overall basis weight reduced to 40 gsm and then again to 31 gsm at binder levels of 10 gsm and 7 gsm, respectively. The material was soft to the touch, fiber formation was greatly improved, and it dispersed quickly in cold tap water.

EXAMPLE 4

A fabric containing 24 gsm of Cemfiber polypropylene (2d/f and 6 millimeters in length) and Rayonier pulp (75:25 blend, respectively) was sprayed with 3.5 gsm of the binder of Example 1 on both sides of the fabric to provide a fabric with overall basis weight of 31 gsm. The material was found to disperse in cold tap water.

EXAMPLE 5

A fabric containing 54.4 gsm of Weyerhauser CF 405 pulp was sprayed on both sides with 6.8 gsm of the binder of Example 1 resulting in an overall basis weight of 68 gsm. The fabric had a density of about 0.1 g/cc. Added to the fabric was 185 weight %, based on the dry weight of the fabric plus binder, of an aqueous solution having a concentration of 100 ppm calcium divalent ions.

A sample of the above saturated fabric having a width dimension of 76 millimeters and a length dimension of 152 millimeters was placed in a Thwing-Albert tensile tester. The tensile strength of the saturated fabric in the cross-machine direction was determined following ASTM-D5034-11 (1994) test procedures. The fabric had a strength of 185 grams.

EXAMPLE 6

A fabric containing 60 gsm of Weyerhauser CF 405 pulp was sprayed on both sides with 7.5 gsm of the binder of Example 1 resulting in an overall basis weight of 75 gsm. The fabric had a density of about 0.1 g/cc. Added to the fabric was 186 weight %, based on the dry weight of the fabric plus binder, of an aqueous solution having 100 ppm divalent ions. The fabric had a strength of 225 grams using the procedure as described in Example 5.

EXAMPLE 7

A fabric containing 50 gsm of Weyerhauser NB-416 pulp was sprayed with 9 gsm of the binder of Example 1 on both sides resulting in an overall basis weight of 68 gsm. The fabric was allowed to age to determine the effect of time on the tensile strength of the fabric. Added to the fabric an aqueous solution having 100 ppm of calcium divalent ions. The fabric was allowed to remain in the solution for the time specified. Samples of the saturated fabric having a width dimension of 25.4 millimeters and a length dimension of 76.2 millimeters were placed in double walled plastic bags and all the edges were heat sealed to prevent evaporation of the solution. Aging was done in an environmentally controlled room at a temperature of 37° Centigrade and a relative humidity of 80%. The samples were tested immediately after removal from the plastic bag. The tensile strength of the saturated fabric, measured in the CD direction, was determined using a Vitrodyne V-1000 Universal Tester available from John Chatillon & Sons, Inc., 7609 Business Park Drive, Greensboro, N.C. The jaw speed of the tester was 3,000 micro meters per second.

The test procedure was repeated on a similar fabric after it had been immersed in tap water for five (5) minutes. Five replications of each were performed and the values were then averaged. The results of the aging test are in Table 1 below.

TABLE 1

| Duration | Strength of fabric (100 ppm calcium ion solution) | Strength of fabric (tap water) |
| --- | --- | --- |
| immediately | 142 grams | 16 grams |
| 1 week | 154 grams | 76 grams |
| 2 weeks | 126 grams | 74 grams |
| 4 weeks | 99 grams | 35 grams |
| 3 months | 118 grams | 47 grams |
| 6 months | 99 grams | 47 grams |

Those skilled in the art will appreciate that various substitutions, omissions, changes and modifications may be made without departing from the spirit of the invention or scope of the appended claims. Accordingly, it is intended that the foregoing description be deemed merely exemplary of the preferred scope of the present invention and not be deemed a limitation thereof.

We claim:

1. A water dispersible fibrous fabric comprising a fibrous substrate and a water-soluble binder distributed through said fibrous substrate, wherein said fabric is water dispersible in an aqueous environment having a divalent ion concentration less than about 50 ppm and a monovalent ion concentration of less than about 0.5 weight %, wherein said binder comprises from about 25 weight % to about 90 weight % of an unsaturated carboxylic acid/unsaturated carboxylic acid ester copolymer; from about 10 weight % to about 75 weight % of a sulfonated copolyester; and from about 0 weight % to about 10 weight % of a plasticizer.

2. The water dispersible fibrous fabric of claim 1, wherein the binder comprises from about 40 weight % to about 75 weight % of the unsaturated carboxylic acid/unsaturated carboxylic acid ester copolymer and from about 25 weight % to about 60 weight % of the sulfonated copolyester.

3. The water dispersible fibrous fabric of claim 1, wherein from about 1 to about 60 mole percent of the unsaturated carboxylic acid portion of the copolymer is neutralized to form a salt.

4. The water dispersible fibrous fabric of claim 1 wherein said fibrous material is a nonwoven fabric.

5. The water dispersible fibrous fabric of claim 1 wherein said fibrous material will disperse in water after 20 minutes.

6. The water dispersible fibrous fabric of claim 1 wherein said fibrous material will disperse in water after 10 minutes.

7. The water dispersible fibrous fabric of claim 1 wherein after 20 minutes said fibrous material breaks up into multiple pieces each having an average size of less than about 50% relative to its pre-dispersed size.

8. The water dispersible fibrous fabric of claim 1 wherein after 20 minutes said fibrous material breaks up into multiple pieces each having an average size of less than about 40% relative to its pre-dispersed size.

9. The water dispersible fibrous fabric of claim 1 wherein after 20 minutes said fibrous material breaks up into multiple pieces each having an average size of less than about 30% relative to its pre-dispersed size.

10. The water dispersible fibrous fabric of claim 1 wherein said fabric is used in a disposable absorbent article.

11. The water dispersible fibrous fabric of claim 10 wherein said disposable absorbent article is a sanitary napkin, a diaper, a wipe, or an incontinence garment.

12. The water dispersible fibrous fabric of claim 1, wherein from about 8 weight % to about 25 weight % of said binder is distributed on said fabric.

13. A water dispersible fibrous fabric comprising a fibrous substrate and a water soluble binder distributed through said fibrous substrate, wherein said fabric is water dispersible in an aqueous environment having a divalent ion concentration less than about 50 ppm and a monovalent ion concentration of less than about 0.5 weight %, wherein said water soluble binder consists essentially of an unsaturated carboxylic acid/unsaturated carboxylic acid ester copolymer and a divalent ion inhibitor, wherein the divalent ion inhibitor is a sulfonated copolyester.

14. The water dispersible fibrous fabric of claim 13, wherein the divalent ion inhibitor is a sulfonated copolyester.

15. The water dispersible fibrous fabric of claim 13, wherein the binder consists essentially from about 25 weight % to about 90 weight % of the unsaturated carboxylic acid/unsaturated carboxylic acid ester copolymer and from about 10 weight % to about 75 weight % of the divalent ion inhibitor.

16. The water dispersible fibrous fabric of claim 15, wherein the binder consists essentially of from about 40 weight % to about 75 weight % of the unsaturated carboxylic acid/unsaturated carboxylic acid ester copolymer and from about 25 weight % to about 60 weight % of the divalent ion inhibitor.

17. The water dispersible fibrous fabric of claim 13, wherein from about 1 to about 60 mole % of the unsaturated carboxylic acid portion of the copolymer is neutralized to a salt.

18. The water dispersible fibrous fabric of claim 13, wherein the fabric is used in a disposable absorbent article, said disposable absorbent article being a sanitary napkin, a diaper, a wipe, or an incontinence garment.

19. A disposable absorbent article comprising a water dispersible fibrous fabric, wherein the fabric comprises:
   a fibrous substrate; and
   a water-soluble binder comprising from about 25 weight % to about 90 weight % of an unsaturated carboxylic acid/unsaturated carboxylic acid ester copolymer; from about 10 weight % to about 75 weight % of a sulfonated copolyester; and from about 0 weight % to about 10 weight % of a plasticizer; wherein said fabric is water dispersible in an aqueous environment having a divalent ion concentration less than about 50 ppm and a monovalent ion concentration of less than about 0.5 weight %.

20. The disposable absorbent article of claim 19, wherein the article is a sanitary napkin, a diaper, a wipe, or an incontinence garment.

21. The disposable absorbent article of claim 19, wherein the binder comprises from about 40 weight % to about 75 weight % of the unsaturated carboxylic acid/unsaturated carboxylic acid ester copolymer and from about 25 weight % to about 60 weight % of the sulfonated copolyester.

22. The disposable absorbent article of claim 19, wherein from about 1 to about 60 mole % of the unsaturated carboxylic acid portion of the copolymer is neutralized to form a salt.

* * * * *